(12) United States Patent
Young et al.

(10) Patent No.: US 11,399,926 B2
(45) Date of Patent: Aug. 2, 2022

(54) MOUTHPIECE FOR DENTAL TREATMENT

(71) Applicant: KONINKLIJKE PHILIPS N.V., Eindhoven (NL)

(72) Inventors: Nigel David Young, Meadvale (GB); Gertrude Riëtte Bakker-Van Der Kamp, Den Helder (NL); Paulus Cornelis Duineveld, Drachten (NL); Olaf Thomas Johan Antonie Vermeulen, Oss (NL); Valentina Lavezzo, Heeze (NL); James Donald Gwyer, Great Chesterford (GB); Zeynep Sabah, Cambridge (GB)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 323 days.

(21) Appl. No.: 16/644,529

(22) PCT Filed: Sep. 6, 2018

(86) PCT No.: PCT/EP2018/073917
§ 371 (c)(1),
(2) Date: Mar. 5, 2020

(87) PCT Pub. No.: WO2019/048509
PCT Pub. Date: Mar. 14, 2019

(65) Prior Publication Data
US 2020/0261197 A1   Aug. 20, 2020

Related U.S. Application Data

(60) Provisional application No. 62/556,560, filed on Sep. 11, 2017.

(51) Int. Cl.
*A61C 19/06*    (2006.01)
*A61N 5/06*    (2006.01)

(52) U.S. Cl.
CPC ............ *A61C 19/066* (2013.01); *A61N 5/062* (2013.01); *A61N 5/0603* (2013.01); *A61N 2005/0606* (2013.01)

(58) Field of Classification Search
CPC ...... A61C 19/06; A61C 19/066; A61N 5/062; A61N 5/0603; A61N 2005/0606
See application file for complete search history.

(56) References Cited

U.S. PATENT DOCUMENTS

| 5,513,984 A | 5/1996 | Ueno |
| 6,280,196 B1 | 8/2001 | Berghash |

(Continued)

FOREIGN PATENT DOCUMENTS

| EP | 1649827 A1 * | 4/2006 | ........... A61C 19/063 |
| EP | 1649827 A1 | 4/2006 | |

(Continued)

OTHER PUBLICATIONS

International Search Report and Written Opinion, International Application No. PCT/EP2018/073917, dated Nov. 14, 2018.

*Primary Examiner* — Jacqueline T Johanas
*Assistant Examiner* — Shannel Nicole Belk

(57) ABSTRACT

The invention relates to a mouthpiece for performing a treatment of teeth such as teeth whitening. Accordingly, the mouthpiece may be arranged for cosmetic treatment. The treatment is based on illumination of the teeth of light with a suitable wavelength. The mouthpiece is designed so that light from light sources, e.g. LED's, is sufficiently homogenized so that the light irradiance at the teeth is sufficiently uniform to achieve good treatment results. Furthermore, the mouthpiece is designed so that the irradiance at the teeth is sufficiently high to achieve efficient treatment and so that heating of the teeth is minimized to an acceptable heating.

12 Claims, 4 Drawing Sheets

(56) References Cited

U.S. PATENT DOCUMENTS

| | | | |
|---|---|---|---|
| 6,616,447 B1 * | 9/2003 | Rizoiu | A61C 19/063 433/29 |
| 7,160,111 B2 | 1/2007 | Baughman | |
| 7,645,137 B2 | 1/2010 | Wasyluch | |
| 8,215,954 B2 | 7/2012 | Jonathan | |
| 8,371,853 B2 | 2/2013 | Levine | |
| 8,591,227 B2 | 11/2013 | Levine | |
| 9,084,657 B2 | 7/2015 | Matty et al. | |
| 2003/0091954 A1 * | 5/2003 | West | A61C 19/003 433/29 |
| 2005/0048444 A1 * | 3/2005 | Creamer | A61Q 11/00 424/53 |
| 2005/0080404 A1 * | 4/2005 | Jones | A61B 18/22 606/16 |
| 2005/0087750 A1 * | 4/2005 | Braddell | F21K 9/00 257/89 |
| 2006/0134576 A1 * | 6/2006 | West | A61C 19/066 433/29 |
| 2007/0009856 A1 * | 1/2007 | Jones | A61C 17/20 433/215 |
| 2008/0032252 A1 | 2/2008 | Hayman et al. | |
| 2008/0063999 A1 * | 3/2008 | Osborn | A61C 19/066 433/29 |
| 2011/0104631 A1 * | 5/2011 | Levine | A61C 19/063 433/29 |
| 2013/0052613 A1 | 2/2013 | Chetiar et al. | |
| 2015/0044628 A1 * | 2/2015 | Flyash | A61C 17/20 433/32 |
| 2015/0064645 A1 * | 3/2015 | Jablow | A61C 1/088 433/29 |
| 2021/0008384 A1 * | 1/2021 | Lee | A61N 5/062 |
| 2022/0000590 A1 * | 1/2022 | Ruth | A61N 5/0603 |

FOREIGN PATENT DOCUMENTS

| | | | |
|---|---|---|---|
| WO | 2004066858 A2 | 8/2004 | |
| WO | WO-2018177832 A1 * | 10/2018 | A61C 1/088 |

\* cited by examiner

MOUTHPIECE FOR DENTAL TREATMENT

This application is the U.S. National Phase application under 35 U.S.C. § 371 of International Application No. PCT/EP2018/073917, filed on 6 Sep. 2018, which claims the benefit of U.S. Provisional Application No. 62/556,560, filed 11 Sep. 2017. These applications are hereby incorporated by reference herein.

FIELD OF THE INVENTION

The invention relates to teeth illumination devices and to oral care or hygiene devices such as teeth whitening devices.

BACKGROUND OF THE INVENTION

Oral care devices such as teeth whitening or oral treatment devices use light for illuminating the teeth. The light can be used for different purposes including teeth whitening in combination with a whitening gel or varnish, plaque or bacteria hygiene by use of disinfecting UV light or other purposes. In order to be effective, the intensity of the light need to be sufficiently high. It is also important that the light has a uniform intensity distribution over the teeth. In order to avoid damage of the pulp in the pulp chamber of the teeth it is also important that heating of the teeth is kept safely below a critical temperature.

Accordingly, there is a need for an oral care device which addresses one or more of these requirements. Accordingly, there is a need for an oral care device which is capable of illuminating the teeth with a sufficiently high intensity, with a uniform intensity distribution, and which only causes acceptable heating of the teeth.

There is also a need for oral care devices for home use. Accordingly, in order to make devices feasible for home use, manufacturing costs may be important and, therefore, a design which enables manufacturing for home use may be needed.

US 2011/0104631A1 discloses a method for effecting an oral treatment of teeth and/or gums using an intra-oral device that has a mouthpiece in which is embedded a flexible circuit board and arrays of spaced apart lamps. The mouthpiece has a curvature. The lamps may be light emitting diodes (LEDs) that generate electromagnetic radiation, preferably in the white and blue light spectrum and the infrared and ultraviolet light spectrum. The arrays are positioned to expose the facial and lingual sides of the teeth and/or gums for effecting the treatment when the mouthpiece is positioned to fit upper and lower rows of teeth within accommodating recesses. The flexible circuit board is flexed to exhibit a curvature that follows a curvature of the mouthpiece. Treatments include whitening teeth, desensitizing teeth, and treating gums to prevent periodontal disease.

The inventor of the present invention has appreciated that an improved mouthpiece for treatment of teeth is of benefit, and has in consequence devised the present invention.

SUMMARY OF THE INVENTION

It would be advantageous to achieve an oral device capable of providing generation of a uniform light intensity at the teeth, and alternatively or additionally capable of reducing heating of the teeth. In general, the invention preferably seeks to mitigate, alleviate or eliminate one or more of the above mentioned disadvantages singly or in any combination.

To better address one or more of these concerns, in a first aspect of the invention a mouthpiece for performing a treatment of teeth is presented, the mouthpiece comprises:
one or more light sources arranged to illuminate teeth,
an optical light distribution unit with an output surface, where the optical light distribution unit is arranged to redirect at least a part of the light rays from the one or more light sources before the lights rays exits through the output surface to the teeth and/or to redirect scattered light rays injected into the optical light distribution unit from the output surface back to the output surface for more uniform illumination,
where the one or more light sources and the optical light distribution unit are arranged to provide an irradiance of the teeth that is equal to or greater than about 20 mW/cm2.

By providing an irradiance which is equal to or greater than about 20 mW/cm2, efficient treatment, such as teeth whitening can be achieved. Possible useful irradiances may be within a range from approximately 20-150 mW/cm2. By configuring the optical light distribution unit to redirect at least a part of the light rays from the light sources before they are emitted towards the teeth, improved uniformity of the irradiance distribution at the teeth is achieved. In one embodiment, by configuring the optical light distribution unit to be transparent, or substantially transparent, the desired irradiance is achieved. By the "at least a part of the light rays" which are redirected may be understood that a substantial percentage of the light rays are redirected such as the light rays corresponding to at least 20% of the light irradiance emitted from the light sources. Other percentages above 20% are also within practical limits of various embodiments, e.g. percentages such as 25-40% or 60-90%.

According to an embodiment, the optical light distribution unit is arranged to provide a minimum optical path length of at least 0.8 mm of the light rays from the one or more light sources to the output surface. By providing an optical path length of sufficient length such as at least 0.8 mm, a certain degree of light mixing of the light rays from the light sources may be achieved which provides improved homogenization. As an effect of the optical path length of at least 0.8 mm, a variation of the light irradiance at the front surface of the teeth may be less than 25 percent relative to mean values of the light irradiance.

According to an embodiment, the optical light distribution unit is arranged to provide a minimum thermal insulance, or resistance of at least 0.001 m2 K/W along a thermal pathway from the one or more light sources to the output surface. Advantageously, the thermal insulance of at least 0.001 m2 K/W reduces heating of the teeth so that the temperature during use of the mouthpiece may be kept below 42 degree Celsius. Furthermore, the thermal insulance improves the uniformity of the heating of the teeth, e.g. so that a temperature variation at the front surface of the teeth of less than 25 percent relative to a mean value of the temperature can be achieved.

According to an embodiment, the optical light distribution unit comprises distance members arranged at the output surface and protruding away from the output surface. The distance members provides a uniform gap between teeth (e.g. when the teeth are not positioned perfectly in an arc shape) and the output surface of the light distribution unit so as to achieve a uniform and controlled thickness of the applied dental substance.

According to an embodiment, the optical light distribution unit comprises a light redirecting structure arranged to redirect at least the part of the light rays from the one or more light sources, wherein at least a part of the light redirecting structure is located between the one or more light sources and the output surface. Advantageously, the light redirecting structure causes light rays to travel a longer distance and therefore improves light mixing of light rays.

According to an embodiment, the mouthpiece comprises a back reflector arranged to redirect the scattered light rays transmitted into the optical light distribution unit via the output surface back to the output surface, where the back reflector extends over at least a portion of a back side of the optical light distribution unit. As a secondary effect, the back reflector also causes redirection of other light rays such as light rays reflected from the a light redirecting structure. The back reflector improves the efficiency of the light sources since light is not lost, but reflected back to the teeth. Furthermore, the back reflector improves light mixing and thereby light homogenization.

According to an embodiment, the optical light distribution unit is arranged to cause total internal reflection of at least a part of the light rays injected into the optical light distribution unit from the one or more light sources so as to redirect at least a part of the light rays from the one or more light sources before the lights rays exit through the output surface. Advantageously, the utilization of total internal reflection improves homogenization of the light.

According to an embodiment, the one or more light sources are mounted on a support structure having a thermal insulance which is lower than the thermal insulance of the optical light distribution unit. The lower thermal insulance improves heat conduction so that more heat energy is transported away from the teeth. Furthermore, the lower thermal insulance may improve homogenization of heat.

According to an embodiment, the one or more light sources are arranged so that neighboring light sources in a row of light sources are separated by at least 3 mm and by at most 8 mm. The range from 3 to 8 mm provides a trade-off between reducing the number light sources and improving light homogenization.

According to an embodiment, the one or more light sources are arranged along at least two rows. The arrangement with at least two rows may be beneficial when the mouthpiece comprises an opaque part which prohibits light transmission between the upper and lower parts of the mouthpiece.

According to an embodiment, the mouthpiece comprises a sealing structure arranged for retaining an applied dental substance within a space defined by the output surface, the sealing structure and the front side of the teeth.

A second aspect of the invention relates to use of a mouthpiece according to the first aspect for treatment of the teeth comprising
applying a dental substance on a surface of the mouthpiece
so that the dental substance contacts the output surface, or applying the dental substance on the front surface of the teeth, and
arranging the mouthpiece so that the output surface faces the front side of the teeth of a user.

According to an embodiment, the dental substance is a gel with a yield stress of at least of 25 Pa. Advantageously, by using a gel with a yield stress of at least of 25 Pa, most of the gel stays in place and with a low loss of gel, e.g. lower than 10%. For example, the gel may stay in place for at least 30 min. during the treatment.

According to an embodiment, the applied dental substance together with the optical light distribution unit provides a minimum optical path length of at least 1 mm of the light rays from the one or more light sources to the front surface of the teeth.

According to an embodiment, the applied dental substance together with the optical light distribution unit provides a minimum thermal insulance of at least 0.001 m2 K/W along a thermal pathway from the one or more light sources to the front surface of the teeth.

In summary, the invention relates to a mouthpiece for performing a treatment of teeth such as teeth whitening. Accordingly, the mouthpiece may be arranged for cosmetic treatment. The treatment is based on illumination of the teeth of light with a suitable wavelength. The mouthpiece is designed so that light from light sources, e.g. LED's, is sufficiently homogenized so that the light irradiance at the teeth is sufficiently uniform to achieve good treatment results. Furthermore, the mouthpiece is designed so that the irradiance at the teeth is sufficiently high to achieve efficient treatment and so that heating of the teeth is minimized to an acceptable heating.

In general the various aspects of the invention may be combined and coupled in any way possible within the scope of the invention. These and other aspects, features and/or advantages of the invention will be apparent from and elucidated with reference to the embodiments described hereinafter.

BRIEF DESCRIPTION OF THE DRAWINGS

Embodiments of the invention will be described, by way of example only, with reference to the drawings, in which.

DESCRIPTION OF EMBODIMENTS

Figure 1:
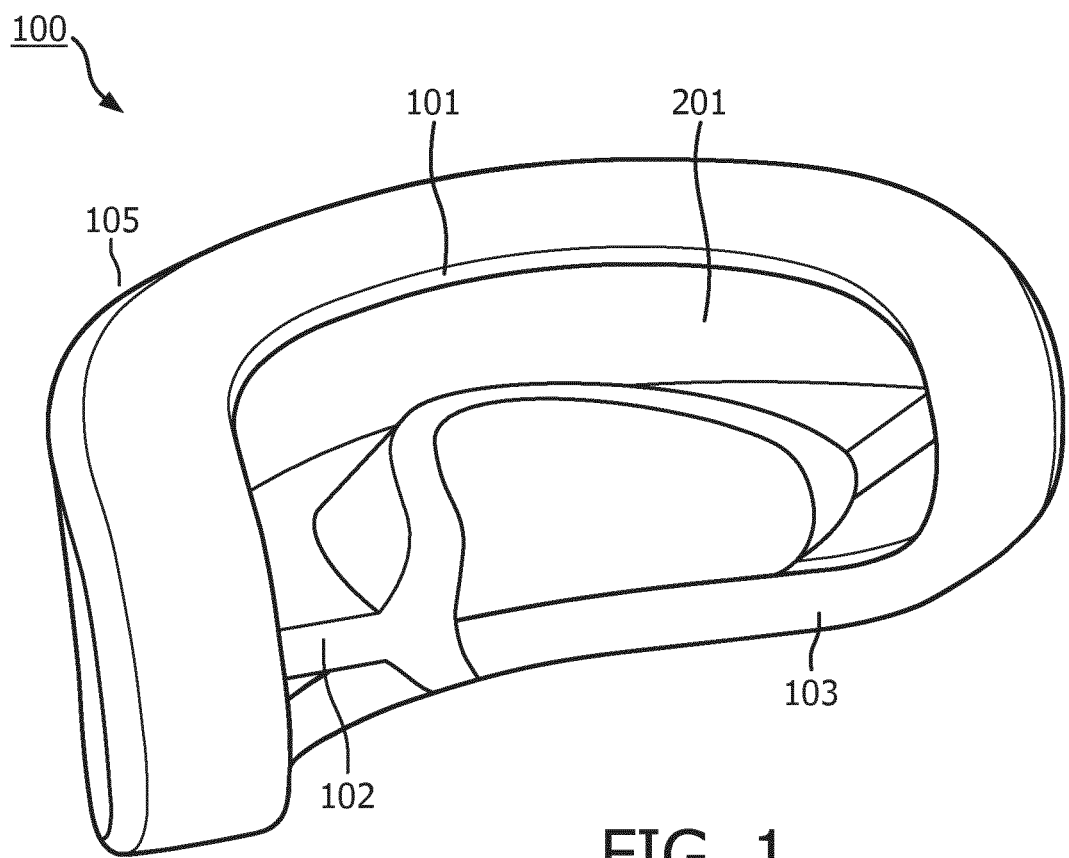
FIG. 1 shows an embodiment of a mouthpiece for treatment of teeth of a user.

FIG. 1 shows an embodiment of a mouthpiece 100 for treatment of teeth of a user. The treatment is performed by illumination of the teeth. The teeth of a user may be illuminated for the purpose of teeth whitening, plaque or bacteria hygiene, or other oral hygiene or care uses. The mouthpiece may be a consumer product for home use or a professional product to be used by a professional, in both cases the user, i.e. the home user or the patient, is the person that receives the illumination from the device.

The mouthpiece 100 comprises an optical light distribution unit 101 arranged to face and to transmit light to the teeth. The optical light distribution unit 101 may be part of body 105 comprised by the mouthpiece 100. Accordingly, the optical light distribution unit may be covered by a surrounding material such as, for example, an optical transparent material of the body 105.

According to an embodiment, the mouthpiece 100 comprises a protruding bite part 102 extending along at least a part of the optical light distribution unit 101. The bite part 102 extends outwardly, e.g. perpendicular to light distribution unit 101, to form bite surfaces, i.e. the illustrated upper and lower planes of the bite part 102. The user can bite onto the upper and lower bite surface so that the upper and lower occlusal sides of the teeth contacts the bite surfaces. In this way the mouthpiece can be held in place in the mouth by applying a force from the teeth to the bite part 102.

The mouthpiece 100 may have a sealing structure 103. The sealing structure 103 may be formed as a rim which at least partly circumscribes the optical light distribution unit 101. For example, the bite part 102 may be circumscribed together with the light distribution unit 101. In another example, the sealing structure 103 may be formed as a rim with openings, e.g. near the end-surfaces of the bite part 102, so that the rim or sealing structure 103 partly circumscribes the light distribution unit 101. The sealing structure 103 may be shaped to contact gums of a user along the upper and lower dental arches. A function of the sealing structure 103 is to serve as a sealing structure for retaining an applied dental substance within a space defined by the light distribution unit 101, the sealing structure 103 and a front surface of the teeth 211 (see FIG. 2). Accordingly, the sealing structure 103 prevents leaking of the dental substance, e.g. teeth whitening gel or other dental substance. The optional bite part 102 may also be seen as a part of the sealing structure 103 since the bite part 102 restrains the location of the dental substance to above or below the occlusal plane.

A further function of the bite part 102 is to retain the shape of the mouthpiece 100 when a force is applied to the mouthpiece 100. E.g. when the mouthpiece 100 is too big for a user, the user applies a pressure to the mouthpiece 100 by means of the bite part 102 so that rim makes contact with the gums.

Figure 2:
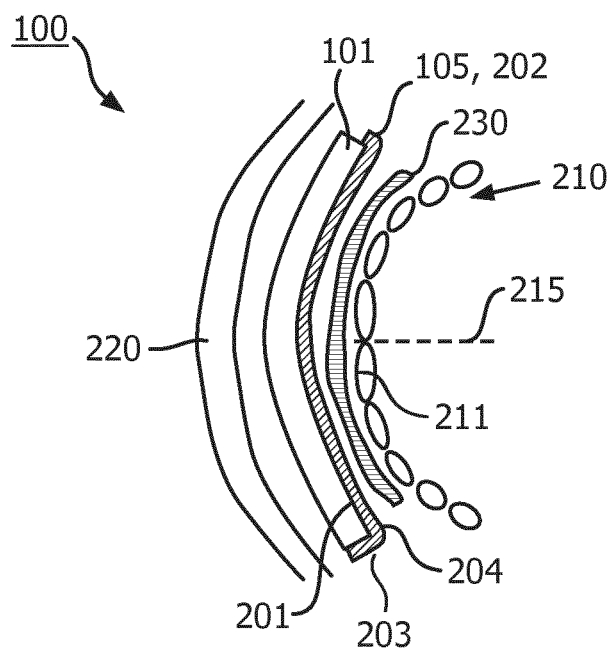
FIG. 2 shows an embodiment of the mouthpiece in a cross-sectional view in a plane parallel with the occlusal plane of the teeth.

FIG. 2 shows an embodiment of the mouthpiece 100 in a cross-sectional view in a plane parallel with the occlusal plane of the teeth 210. The teeth 210 have a front surface 211 which faces the optical light distribution unit 101 and an opposite back surface. The front surface 211 includes the labial surface of the anterior teeth. The labial surface may include the six or eight teeth closest to the dental midline 215 in the upper and lower jaws (i.e. 12 or 16 teeth in total). According to an embodiment, the mouthpiece 100 is arranged for treatment of the labial surface of the teeth. Thus, the mouthpiece 100 may be arranged to illuminate the labial surface of the teeth such as the front most 8 top and 8 bottom teeth.

The optical light distribution unit 101 has an output surface 201 facing the front surface 211 of the teeth 210. According to some embodiments, the optical light distribution unit 101 comprises a surrounding object 202 which at least partly surrounds the light distribution unit 101. The surrounding object 202 may be a part of the body 105. At least the portion of the surrounding object 202 located between the output surface 201 and the teeth 210 is sufficiently transparent to enable transmission of light from the output surface 201 of the light distribution unit 101 to the teeth. The optical light distribution unit 101 and the surrounding object 202 constitute an optically transmissive part 203 which has an output surface 204 adjacent to the output surface 201.

However, according to other embodiments, the optical light distribution unit 101 is not covered at the output surface 201 by a surrounding object 202, or the optical light distribution unit 101 and surrounding object 202, are made from the same material or different material, and constitute an optical light distribution unit 101. Therefore, the optically transmissive light distribution unit 101 includes the surrounding object 202 for embodiments where the surrounding object is an optically transmissive object connected with the output surface 201. For such embodiments, the output surface 204 of the surrounding object 202 or the optically transmissive part 203 is equivalent to the output surface 201.

The optical light distribution unit 101 may be made from flexible materials like silicone or polysiloxane polymers. In another example, the optical light distribution unit 101 is made from polycarbonate. Alternative materials for the light distribution unit 101 includes polymethylmethacrylat, thermal plastic elastomers (TPE), cyclic-olefin polymers, cyclic-olefin copolymers, polyetherimide, styrene and polyesters like OKP-4

The optical light distribution unit 101 may be referred to as a transparent part, i.e. transparent in the sense the light is not scattered in the optically transparent element. However, in practice the transparent material may contain irregularities, e.g. particles, implying that some light scattering will take place. In other examples, scattering particles are deliberately included in the optical light distribution unit 101. Accordingly, the optically transparent element may be referred to as an optically translucent element or an optically transmissive element. The optical light distribution unit 101 should be made of a material that is sufficiently optically transmissive that light rays conveyed from the light source to the teeth 210 provides the desired uniform light output level at the teeth surface. By configuring the optical light distribution unit to be transparent, or substantially transparent, the desired irradiance may be achieved. By configuring the optical light distribution unit to redirect at least a part of the light rays from the light sources before they are emitted towards the teeth, improved uniformity of the irradiance distribution at the teeth is achieved.

By providing an irradiance which is equal to or greater than about 20 mW/cm2, efficient treatment, such as teeth whitening can be achieved. Possible useful irradiances may be within a range from approximately 20-150 mW/cm2. In order to achieve effective treatment, it is also important that the irradiance be substantially uniform across the entire area of the teeth being treated, rather than having a much higher intensity in certain illuminated areas and significantly less intensity in other areas. The mouthpiece of the present invention has been designed to provide a more uniform light intensity at the treatment surface. It has been found that for treatment efficiency, at least approximately 65% of the treatment surface should have an irradiance intensity at the treatment surface that deviates from the desired intensity by no more than 25%, and for optimal treatment efficiency, at least approximately 75% of the treatment area should have an irradiance intensity that deviates from the desired intensity by no more than 15%. So, for example, if the desired irradiance at the treatment surface (i.e. the tooth surface) is 20 mW/cm2, then at least 65% of the treatment surface should receive a light intensity that is between approximately 15-25 mW/cm2 (+/−25% of the desired 20 mW/cm2), and at least 75% of the treatment surface should receive a light intensity that is between approximately 17 mW/cm2 and 23 mW/cm2.

As shown in FIG. 2, the optical light distribution unit 101, as well as other parts of the mouthpiece 100 such as the bite part 102, the sealing structure 103 and other parts of the body 105 is intended to be placed between the front surface of the teeth 211 and the lips 220. The one or more light sources may be placed between the front surface of the teeth 211 and the lips 220 together with the optical light distribution unit 101. Alternatively, the one or more light sources may be placed outside of the lips, with the light directed into the interior of the user's mouth toward the optical light distribution unit 101. Accordingly, the mouthpiece 100 is for in-mouth use. A power source such as a battery or power supply for supplying electric power to the light sources may also be placed outside of the mouth, e.g. in a unit directly attached to the in-mouth part of the mouthpiece 100 or via an electrical cord to the in-mouth part of the mouthpiece 100.

FIG. 2 also illustrates a dental substance 230 applied between the front surface 211 of the teeth and the output surface 201 of the light distribution unit 101 or the output surface 204 of the surrounding object 202.

FIG. 2 does not illustrate the one or more light sources comprised by the mouthpiece 100 and arranged to illuminate the teeth 210. The one or more light sources can be arranged in different ways. In general, the optical light distribution unit 101 and the light sources are arranged so that at least a part of the light rays from the one or more light sources are redirected, e.g. by the light distribution unit 101, a component comprised by or connected with the light distribution unit 101. In this way, at least a part of the light rays from the light sources are redirected in the optical path between the light sources and the output surface 201, i.e. before the lights rays exit through the output surface 201 to the teeth 210. Alternatively or additionally, the light distribution unit 101 is arranged so that reflected or scattered light rays from the front surface 211 of the teeth 210, i.e. light which is initially transmitted from the light sources through the output surface 201 towards the teeth 210 and afterwards reflected back into the optical light distribution unit 101, is redirected back to the output surface 201. The initially transmitted rays from the light sources may or may not be direct light rays, i.e. may or may not have been redirected before exiting the output surface 201.

In order to provide a power of light at the teeth which is sufficiently high to enable the desired treatment of the teeth, the one or more light sources should provide an irradiance at the front surface of the teeth 211 which is greater than approximately 20 mW/cm2. According, to an embodiment, the irradiance may be in the range from approximately 20 mW/cm2 to 150 mW/cm2. Alternative lower irradiance values include 30, 40 or 50 mW/cm2. Alternative higher irradiance values include 60, 70, 80 or 90 mW/cm2, although values above 100 mW/cm2 are also possible, such as 110, 120 or 130 and up to 150 mW/cm2. The irradiance used is a trade-off between effective treatment and heating of the teeth. It is important that the teeth are not heated too much and preferably, the temperature should not rise above 42.5 degree Celsius, or preferably not above 42 degree Celsius. Therefore, irradiances below 100 mW/cm2 may be preferred.

Figure 3A:
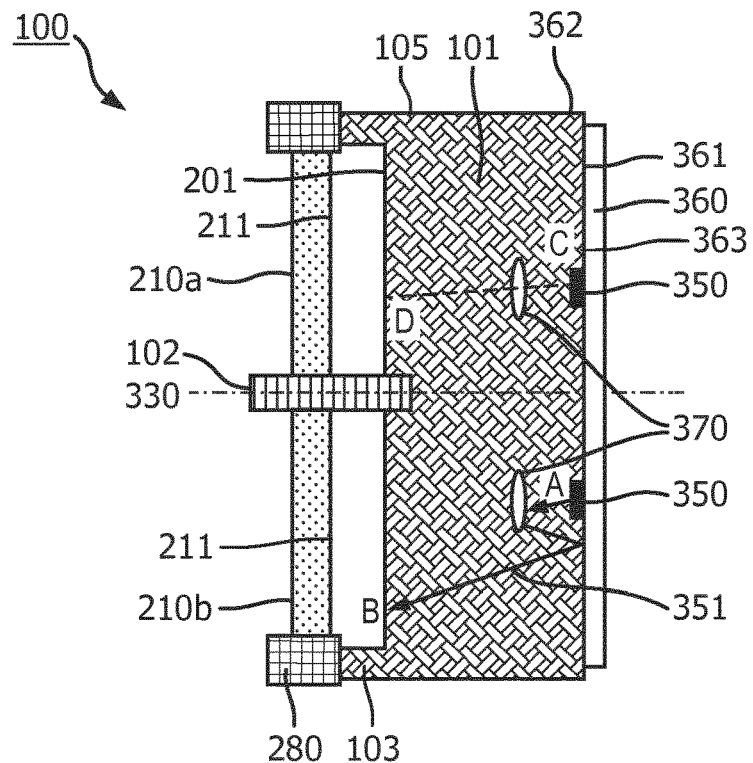
FIG. 3A shows an embodiment of the mouthpiece in a cross-sectional view in a plane perpendicular to the occlusal plane.

FIG. 3A shows a principal sketch of an embodiment of the mouthpiece 100 in a cross-sectional view in a plane perpendicular to the bite surface of the bite part 102, i.e. in a plane perpendicular to the occlusal plane 330, e.g. a plane comprising the dental midline. In this embodiment, the body 105 of the mouthpiece 100 comprises the bite part 102 which extends into the mouth between the upper teeth 210a and the lower teeth 210b. The bite part 102 may be made of a different material then the material of the body 105 or the light distribution unit 101, e.g. an opaque material. Alternatively, the bite part 102 may be made of the same material as the body 105 or the light distribution unit 101, possibly provided with an opaque surface coating. The body 105 comprises the optical light distribution unit 101 and the sealing structure 103. The sealing structure 103 contacts the gums 280 at the upper and lower dental arches. The sealing structure 103 may be made of the same material as the light distribution unit 101 or a different material. For example, the sealing structure 103 may be made from a material which is reflective or has a reflective surface to redirect light back to the treatment surface and away from surfaces that are not being treated, such as the gums 280, in this case. For example, the sealing structure 103, or a portion thereof, can be made from a material that is optically reflective, such as silicone or TPE filled with titanium dioxide (TiO2).

FIG. 3A shows the one or more light sources 350. The light sources 350 may be arranged as shown in a first row extending along the light distribution unit 101 to illuminate mainly the front side 211 of the upper teeth 210a, and in a second row extending along the light distribution unit 101 to illuminate mainly the front side 211 of the lower teeth 210b. Each row may contain one or more light sources 350. For example, the light sources 350 may be arranged so that neighbor light sources in a row of light sources are separated by at least 3 mm and by at most 8 mm.

The light sources 350 may be mounted on a support structure 360, e.g. a printed circuit board which provides electrical connections for the light sources 350. The support structure 360 may have a thermal insulance which is lower than the thermal insulance of the optical light distribution unit 101. The lower thermal insulance improves heat conduction so that heat from the light sources is transferred away from teeth 210. Additionally, the lower heat insulance may improve heat distribution to reduce formation of thermal hot spots at the teeth, i.e. the lower thermal insulance may improve the uniformity of the heating of the teeth.

According to this embodiment, the optical light distribution unit 101 is arranged to redirect at least a part of the light rays from the one or more light sources 350 by means of a light redirecting structure 370 which is arranged to change the propagation direction of the light from the one or more light sources 350. The light redirecting structure(s) 370 may be configured in various ways, but so that at least a part of the light redirecting structure 370 is located between the one or more light sources 350 and the output surface 201. As illustrated in FIG. 3A, the redirecting structure 370 is opaque and has a specular reflective or diffuse reflective surface so that the light from one of the light sources is redirected through specular reflection or scattering. The light redirecting structure 370 could also be semi-transparent and have scattering properties, e.g. embodied by a transparent material filled with scattering particles. As another example, the light redirecting structure 370 could be transparent and arranged to redirect light through refraction. Thus, in general the one or more light sources 350 are arranged relative to the light redirecting structure 370 where the redirecting structure 370 has an extension so that at least some of the emitted light from a light source 350 is redirected by an oppositely located redirection structure 370. Depending on at least the extension of the redirecting structure and the divergence of light from the light sources 350, it is possible that not all light from a light source is redirected, but preferably most of the light hits the redirection structure 370.

In effect, the light redirection structure 370 may force light rays from light sources 350 to travel a longer distance before they escape from the output surface 201, and, as a consequence of this, the intensity distribution at the teeth will be more uniform and less sensitive to distance variations so that the light intensity distribution on teeth is largely maintained and/or so that the intensity on the teeth becomes less sensitive to distance variations between the teeth and output surface 201 due to natural variations in user's oral cavity shapes and variations in the placement of the mouthpiece. One redirected light ray 351 is illustrated in FIG. 3A.

According to an embodiment, the optical light distribution unit 101 is arranged so that the minimum optical path length of a light ray is at least 0.8 mm from a light source (e.g. from A) to the output surface where the light ray leaves the output surface 201 (e.g. to B). Thus, according to this embodiment, all light rays from the light sources 350 will experience an optical path length of a light ray that is at least 0.8 mm. The optical path length is the geometric path length traveled from A to B multiplied by the refractive index of the material of the opticallight distribution unit 101.

Due to the minimum optical path length of a light ray of at least 0.8 mm, the variation of the light intensity at the front surface 211 of the teeth 210 may be less than plus/minus 25 percent relative to a mean value of the light intensity over an area of the front surface 211.

The light sources 350 may be placed with an objective to maximize to the thermal insulance along a thermal pathway from the one or more light sources 350 to the output surface 201, e.g. a thermal pathway from A to B or C to D. By maximizing the thermal insulance, the heat isolation between the light sources 350 and the teeth 210 is improved. This reduces the heating of the teeth due to heat from the light sources 350 and also improves the uniformity of light and heat at the teeth 210.

The placement of the light sources at the back surface 361 ensures that the entire thickness of the optical light distribution unit 101 contributes to maximizing to the thermal insulance.

According to an embodiment, the optical light distribution unit 101 is arranged, i.e. by means of the placement of light sources 350 and the thickness of the optical light distribution unit 101 between the light sources 350 and the output surface 201, to provide a minimum thermal insulance (resistance) of at least 0.001 m2 K/W along a thermal pathway from the one or more light sources 350 to the output surface 201.

Due to the minimum thermal insulance of at least 0.001 m2 K/W, the temperature at the teeth 210 may be kept below approximately 42 degree Celsius during use of the mouthpiece with the irradiance levels described above. Furthermore, with this thermal insulance, the temperature variations at the teeth may be reduced and possibly kept below plus/minus 25 percent relative to a mean values of the temperature at an area of the teeth.

The support structure 360 may function as a back reflector 363 arranged to reflect light rays. Alternatively, other arrangements may be provided to provide reflection of the light rays and to embody the back reflector. For example, the back surface 361 and/or edge surfaces 362 may be provided with white paint or an exterior reflective part in order to reflect incident rays. The back reflector 363 may be extended to other surfaces such as the edge surfaces 362.

The back reflector 363 redirects scattered light rays from the teeth 210 into the optical light distribution unit from the output surface back to the output surface. Therefore, the back reflector 363, together with the reflective surface of the teeth 210 functions to increase the optical path length. Thus, the arrangement of the light distribution unit 101 to redirect the scattered light rays transmitted into the optical light distribution unit 101 back to the output surface may be embodied by the back reflector 363. The back reflector is arranged to that it extends over at least a portion of a back surface or back side 361 of the optical light distribution unit 101.

The mouthpiece 100 may comprise the redirection structures 370, the back reflector 363 or both the redirection structures 370 and the back reflector 363.

The one or more light sources 350 could be arranged at other surfaces of the light distribution unit 101, e.g. at the edge surface 362. In general the one or more light sources 350 could be located at any surface or embedded in the optical light distribution unit 101. Alternatively, the light sources 350 may be arranged external to the light distribution unit 101, such that they are positioned outside the mouth of the user, and directed into the mouthpiece 100 by means such as a light pipe, optical fibre or other methods.

The bite part 102 may be optically isolated from the light distribution unit 101 so that light from light distribution unit 101 is prohibited from entering into the bite part 102.

A dental substance 230 is not illustrated in FIG. 3A, but could be placed between the teeth 210, the output surface 201 and the optional bite part 102. FIG. 3A also does not show the optional surrounding object 202. Thus, at least a part of the light distribution unit 101 could have been covered by a surrounding object 202.

Figure 3B:
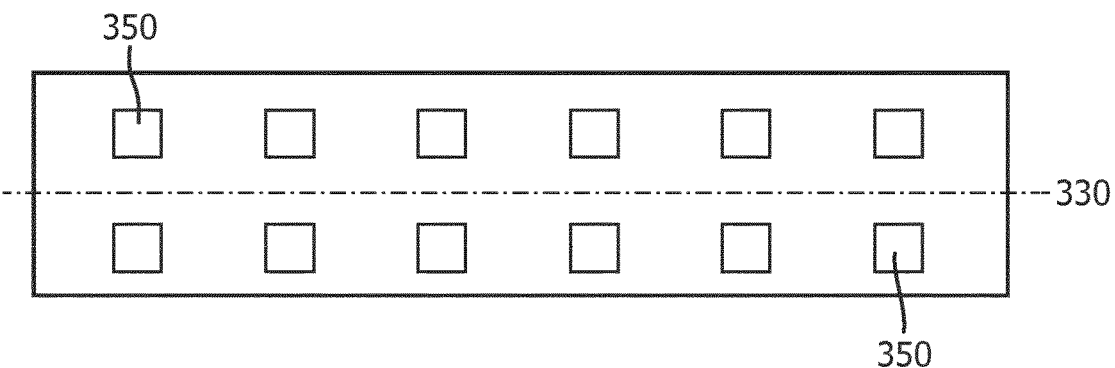
FIGS. 3B-3C show possible configurations of light sources.

FIG. 3B shows, in a schematic illustration of one arrangement of a light distribution unit seen from the back side 361, a possible arrangement of light sources 350. This arrangement of light sources in two rows, with one row of light sources 350 above the occlusal plane 330 and one row of light sources 350 below the occlusal plane 330 may be preferred when the mouthpiece 100 includes an opaque bite part 102.

Figure 3C:
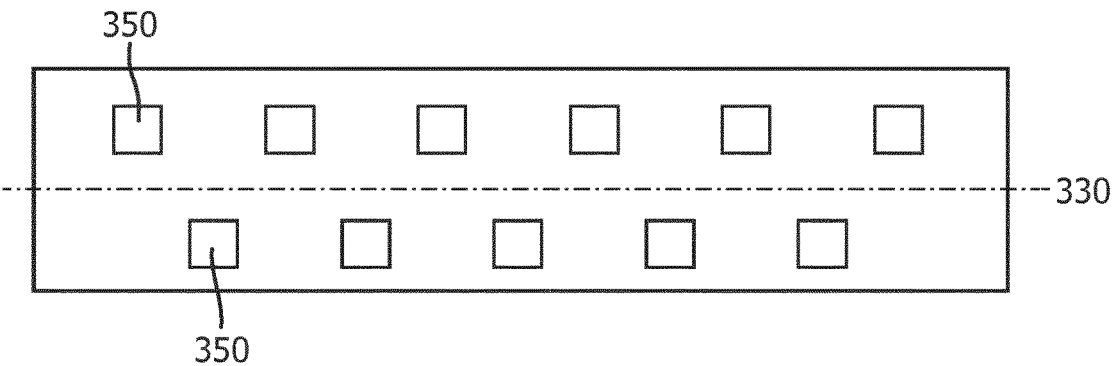

FIG. 3C shows a similar schematic illustration of the arrangement of light sources 350. This arrangement includes one row of light sources 350 above the occlusal plane and one row below the occlusal plane 330, where the light sources 350 in one row is staggered relative to the light sources 350 in another row. This configuration improves the uniformity of the light distribution and may be particularly preferred when the mouthpiece 100 does not include an opaque bite part 102.

Clearly, the light sources 350 could be arranged staggered or non-staggered in more or less than two rows.

Figure 4:
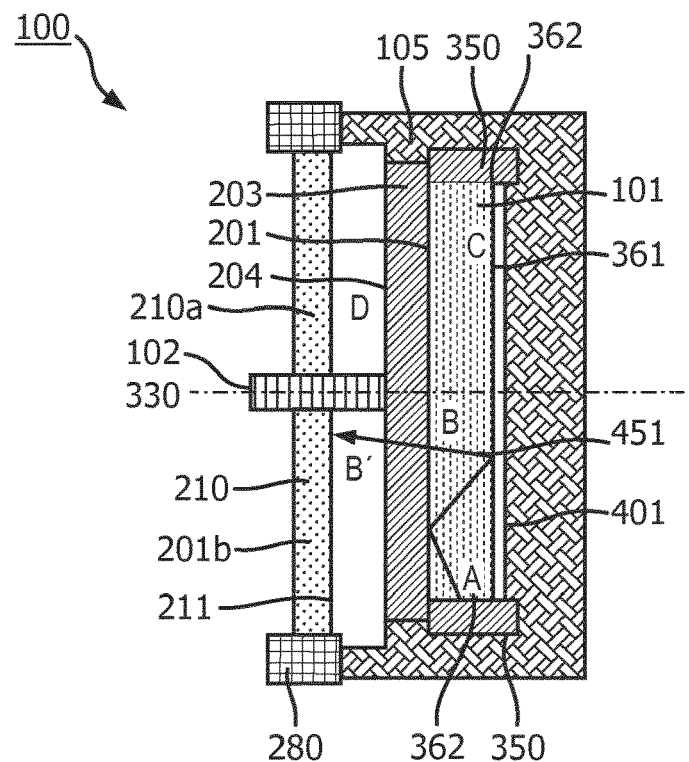
FIG. 4 shows another embodiment of the mouthpiece based on total internal reflection.

FIG. 4 shows a principal sketch of another embodiment of the mouthpiece 100 in a cross-sectional view in a plane perpendicular to the bite surface of the bite part 102, i.e. in a plane perpendicular to the occlusal plane 330.

FIG. 4 shows an optically transparent light distribution unit 101. In this embodiment the light distribution unit 101 has the function of a light guide extending along an optically transparent element 203, an example of the surrounding object 202 (not shown). One or more light sources 350 are arranged for injecting light into the light distribution unit 101. The light sources 350 may be arranged along one or more side edges of the light distribution unit 101, e.g. along the upper and lower edge surfaces 362. The optically transparent element 203 and possibly other parts of the body 105 contacts one or more outer surfaces of the light distribution unit 101.

The light distribution unit 101 has a refractive index which is higher than the refractive index of optically transparent element 203 and possibly other parts of the body 105 which contacts surfaces of the light distribution unit 101. Therefore, the light distribution unit 101 in combination with the surrounding parts enables total internal refection of the reflected light rays 451. For example, the light distribution unit 101 may be made from polycarbonate which has a higher refractive index than the material of surrounding parts. Alternative materials for the light guide includes polymethylmethacrylat, cyclic-olefin polymers, cyclic-olefin copolymers, polyetherimide, styrene and polyesters like OKP-4. Alternatively, the optically transparent element 203 and possibly other parts of the body 105 may be configured so that at least the optically transparent element 203 is separated from the light distribution unit 101 by air gaps at certain areas. According to this alternative, the low refractive index of air enables use of other materials for the light distribution unit 101, e.g. materials like silicone.

Accordingly, the optical light distribution unit 101 is arranged to redirect at least a part of the light rays from the one or more light sources 350 before the lights rays exits through the output surface by means of the capability to cause total internal reflection. The minimum angle on incidence required for generating total internal reflection is governed by known optical laws. The angle of incidence is defined as the angle between the incident light ray and the normal to the surface at the point of incidence.

The bite part 102 may be configured similarly to other embodiments described herein.

In order to couple light out of the light guide towards the teeth 210, the mouthpiece 100 further comprises an out-coupling structure 401 arranged to redirect light in the light guide. The out-coupling structure 401 may be arranged at the back surface 361, e.g. in the form of a paint such as white paint applied to the back surface 361. Alternatively, the out-coupling structure can be realized by making the second surface rough, e.g. by etching or sandblasting the back surface 361. Some of the light rays 451 redirected by the out-coupling structure have an angle relative to the output surface 201 which is large enough to be coupled out through refraction, while other redirected rays 201 have an angle which is sufficiently oblique to be internally reflected.

Similarly to the light redirection structure or the back reflector, the total internal reflection of the light distribution unit 101 forces light rays from light sources 350 to travel a longer distance before they escape from the output surface 201 and, therefore, achieves the same effects with respect to uniformity of light. Furthermore, due to the location of the light sources 350 at the edges, the thermal insulance and distance from the light sources to the teeth 210 is also sufficient to achieve avoid thermal hot spots and temperatures at the teeth 210 above approximately 42 degree Celsius.

Similarly to the embodiment in FIG. 3A, the minimum optical path length of a light ray is at least 0.8 mm from a light source 350 to the output surface 201 of the light distribution unit 101 or the output surface 204 of the optically transparent part 203, i.e. from A to B or B' as illustrated in FIG. 4. Thus, a variation of the light intensity at the front surface 211 of the teeth 210 may be less than plus/minus 25 percent similarly to other embodiments.

Furthermore, the placement of the light sources 350 provides a thermal pathway from C to D which provides a thermal insulance greater than 0.001 m2 K/W so that the temperature at the teeth 210 may be kept below 42 degree Celsius with the irradiance levels described above, and so that the temperature variations can possibly be kept below plus/minus 25 percent relative to a mean values.

During use, if a dental substance 230 (not shown in FIG. 4) is applied, the thickness of the dental substance 230 contributes to optical path length so that the minimum optical path length from the one or more light sources 350 to the front surface 211 of the teeth 210 is at least 1 mm. For example, if the dental substance is a gel with thickness of 0.1 mm, the light distribution unit 101 is made of silicone with a refractive index of 1.43 and the minimum distance from the light sources 350 to the output surface 201 is 0.6 mm, an optical path length of 1 mm is obtained.

Similarly, the thickness of the dental substance 230 contributes to the thermal insulance along the thermal pathway from the one or more light sources 350 to the front surface 211 of the teeth 210 so that the minimum thermal insulance is as least 0.001 m2 K/W or slightly greater than 0.001 m2 K/W.

Figure 5:
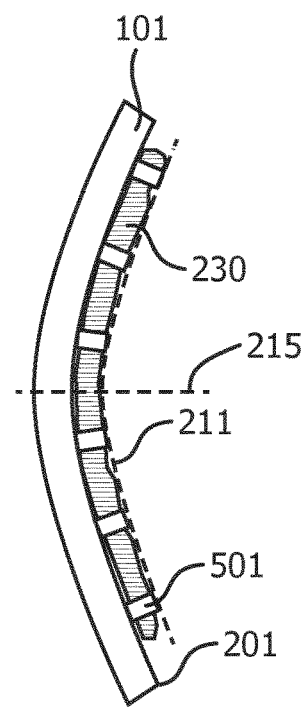
FIG. 5 shows a configuration of the mouthpiece with distance members arranged for contacting the teeth.

FIG. 5. illustrates an embodiment where the optical light distribution unit 101 comprises distance members 501 arranged at the output surface 201 and protruding away from the output surface 201. The illustration is shown in a cross-sectional view in a plane parallel with the occlusal plane of the teeth 210. During use the distance members 501 contacts the front surface 211 of the teeth 210. As defined above, the output surface 204 of the optional surrounding object 202 such as the optical transparent part 203 is equivalent with the output surface 201 of the light distribution unit 101. Therefore, it is understood that the distance members 501 could protrude from the surrounding object 202 (not shown) equivalently.

The function of the distance members 501 is avoid that the teeth create a large contact surface with the output surface 201 of the light distribution unit 101, instead leaving a more uniform space for the applied dental substance 230 to contact the front surface 211 of the teeth. A further function of the distance members 501 is ensure a uniform thickness of the applied dental substance 230.

The distance members 501 may be shaped as pillars, i.e. as two-dimensional structures. The two-dimensional structures may have a flat or rounded top, i.e. inwardly or outwardly rounded top. Alternatively, the distance members 501 may be formed as protruding ridges, e.g. as one-dimensional linear ridges.

The surface area of the base of the distance members 501 may be larger than the surface area of top to prevent the spacers from bending away when pressed against the teeth 210. The diameter or lateral dimension of the top of the distance members 501 may be in the range of of 0.1 to 5 mm, more preferably in the range of 0.5 to 1.5 mm. The height of the distance members may be in the range of 0.2 mm to 5 mm, preferably in the range of 0.5 to 1.5 mm. The distance members may be arranged with a density of 0.5% to 50%, preferably in the range of 1% to 10%. The distance members 501 may be made of different material than light distribution unit 101 or the surrounding object 202. For example, the distance members 501 may be made of material that is optically reflective for instance silicone or TPE filled with TiO2 particles.

The dental substance used may be a teeth-whitening substance such as teeth-whitening gel or varnish. Gels may be preferred due to the capabilities of the gel to stick to the teeth. Preferably, the gel has a yield stress of at least of 25 Pa. The gel may contain in the range from 6-10% hydrogen peroxide to ensure tissue safety when used in single treatment times of up to 60 min. The gel may have pH acidity of 4-8. The dental substance 230 may comprise reflecting particles such as mica, in order to enhance light scattering and uniformity of the light field at the tooth surface.

Figure 6:
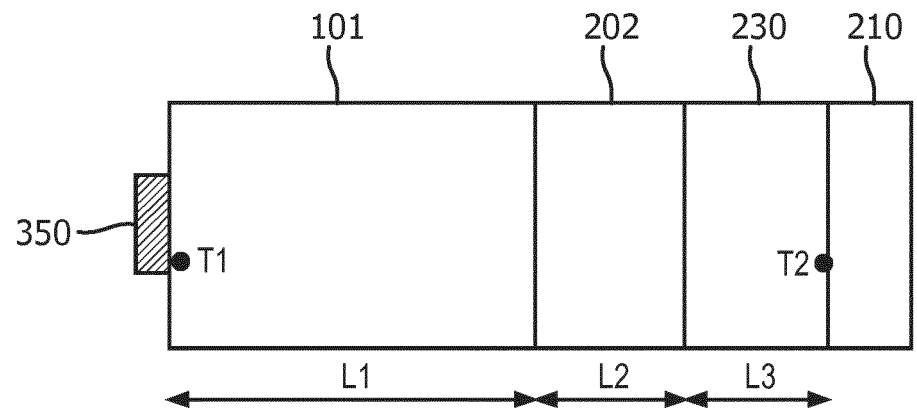
FIG. 6 shows a schematic for determination of thermal insulance and temperature differences.

FIG. 6 schematically illustrates a cross-sectional view of a cut-out portion of different embodiments of the mouthpiece 100. The cross-sectional view is selected so that the distance from the light source 350 to the teeth 210 represents a minimum geometrical path length over other geometric path lengths between light sources 350 and teeth 210. Thus, FIG. 5 illustrates a light source 350 arranged at a surface of the optical light distribution unit 101 or otherwise arranged to emit light into the light distribution unit 101. The light distribution unit 101 may be covered by a the surrounding object 202. A layer of the dental substance 230 may be provided between the teeth 210 and the output surface 201 of the light distribution unit 101 or the surrounding object 202. The light distribution unit 101, the surrounding object 202 and the dental substance 230 have lengths L1, L2 and L3, respectively.

The thermal insulance Ri, i.e. the thermal resistance of unit area of a material, is determined from Ri=L1/λ1+L2/λ2+L3/λ3, where λ1,2,3 is the thermal conductivity of the material associated with the thickness. In case where one of the materials is not part of the geometric pathway, the corresponding term in the sum is simply removed.

Assuming a total thickness of L1=0.6 mm corresponding to an optical path length of approx. 0.8 mm in an embodiment without the surrounding object 202, the thermal insulance Ri=0.6 mm/0.3 W/mK=0.002 (m^2 K)/W. In this case silicone with λ=0.3 W/mK is used for the light distribution unit 101.

Examples of thermal resistance for other materials includes:
λ for PMMA=0.167-0.25 W/mK,
λ for Cyclic Olefin CoPolymer (COP or COC)=0.12-0.15 W/mK,
λ for Polycarbonate (PC)=0.19-0.22 W/mK,
λ for Polyester=0.17 W/mK,
λ for Glass=0.17-0.8 W/mK,
λ for Silicone=0.3 W/mK,
λ for gel types of the dental substance 230=approx. 0.06 W/mK.

Thus, a layer of whitening gel with a thickness of 0.1 mm would contribute with an additional thermal insulance Ri of 0.0016 (m^2 K)/W.

These numbers and calculations support that the minimum thermal insulance is as least 0.001 m2 K/W for various embodiments.

The light sources 350 may optionally emit light in the spectral range from 440 to 500 nm, preferably in the range 440 to 470 nm, e.g. 456 nm. The light sources preferably has an efficiency greater than 40%.

Based on the minimum irradiance Ir of 20 mW/cm2=200 W/m2 it is possible to determine the temperature T1 near the light source assuming a tooth temperature T2 of 42.5 degree Celsius. This can be determined from:

$T1 = Ir \, Ri + T2$, with temperatures in Kelvin.

Based on an example where the mouthpiece 100 comprises a light distribution unit 101 made from silicone with a thickness of 0.6 mm without a surrounding object 202, the temperature T1 for a max tooth temperature T2 of 42.5 degree Celsius is determined to be approx. 43 degree Celsius (based on the above equation and numbers). This shows that with an irradiance of 20 mW/cm2 this does not produce temperatures at the teeth above 42.5 degree Celsius.

Figure 7:
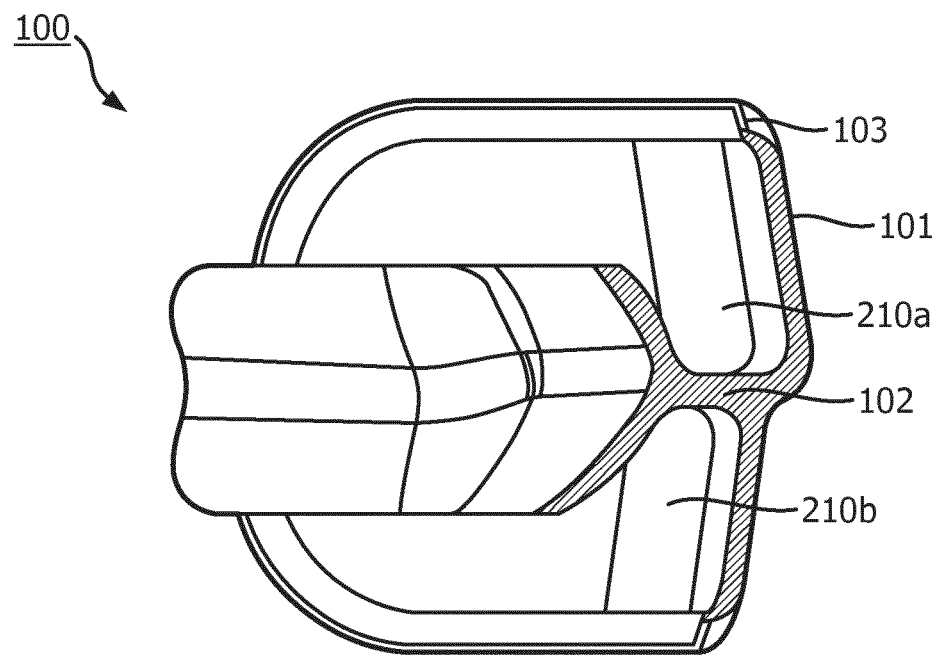
FIG. 7 shows a cut-away side view configuration of the mouthpiece.

FIG. 7 shows an embodiment of the mouthpiece 100 in a perspective cut-out view. FIG. 7 shows the optical light distribution unit 101, the bite part 102 and the sealing structure 103. As illustrated, the upper and lower portions of the mouthpiece 100 can be displaced relative to each other so that the upper portion allows the user to push the upper teeth 210a forward relative to the lower teeth 210b. By shaping the mouthpiece 100 so that the user can position his teeth in a normal "overbite" the comfort for the user may be improved. Furthermore, the walls of the upper and lower portions of the mouthpiece may be angled inwardly towards the teeth 210 to improve the uniformity of the distribution of dental substance 230 (not shown).

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A mouthpiece for performing a treatment of teeth, the mouthpiece comprising:
one or more light sources arranged to illuminate teeth,
an optical light distribution unit with a output surface, where the optical light distribution unit is arranged to redirect at least a part of the light rays from the one or more light sources before the lights rays exits through the output surface to the teeth and/or to redirect scattered light rays injected into the optical light distribution unit from the output surface back to the output surface,
wherein the one or more light sources and the optical light distribution unit are arranged to provide an irradiance of the teeth greater than 20 mW/cm$^2$, and
wherein the optical light distribution unit is arranged to provide a minimum thermal insulance of at least 0.001 m$^2$ K/W along a thermal pathway from the one or more light sources to the output surface.

2. A mouthpiece according to claim 1, where the optical light distribution unit is arranged to provide a minimum optical path length of at least 0.8 mm of the light rays from the one or more light sources to the output surface.

3. A mouthpiece according to claim 1, where the optical light distribution unit comprises distance members arranged at the output surface and protruding away from the output surface.

4. A mouthpiece according to claim 1, wherein the optical light distribution unit comprises a light redirecting structure arranged to redirect at least the part of the light rays from the one or more light sources, wherein at least a part of the light redirecting structure is located between the one or more light sources and the output surface.

5. A mouthpiece according to claim 1, which comprises a back reflector arranged to redirect the scattered light rays transmitted into the optical transparent light distribution unit via the output surface back to the output surface, where the back reflector extends over at least a portion of a back side of the optical transparent light distribution unit.

6. A mouthpiece according to claim 1, wherein the optical light distribution unit is arranged to cause total internal reflection of at least a part of the light rays injected into the optical transparent light distribution unit from the one or more light sources so as to redirect at least a part of the light rays from the one or more light sources before the lights rays exits through the output surface.

7. A mouthpiece according to claim 1, wherein the one or more light sources are mounted on a support structure having a thermal insulance which is lower than the thermal insulance of the optical light distribution unit.

8. A mouthpiece according to claim 1, wherein the one or more light sources are arranged so that neighbor light sources are separated by at least 3 mm and by at most 8 mm.

9. A mouthpiece according to claim 1, wherein the irradiance at the output surface is substantially uniform, such that the irradiance at 65% of the illuminated teeth deviates from the desired irradiance by no more than 25% and the irradiance at 75% of the illuminated teeth deviates from the desired intensity by no more than 15%.

10. A mouthpiece according to claim 1, wherein the optical light distribution unit is transparent.

11. A mouthpiece according to claim 1, comprising a sealing structure arranged for retaining an applied dental substance within a space defined by the output surface, the sealing structure and a front side of the teeth.

12. A mouthpiece according to claim 11, wherein the sealing structure is made from a material which is reflective to redirect light back to the front side of the teeth.

* * * * *